United States Patent
Lan et al.

(10) Patent No.: US 12,054,879 B2
(45) Date of Patent: Aug. 6, 2024

(54) ODOR CONTROL COMPOSITION AND TREATMENT METHOD

(71) Applicant: Microban Products Company, Huntersville, NC (US)

(72) Inventors: Tian Lan, Huntersville, NC (US); Brian Patrick Aylward, Concord, NC (US)

(73) Assignee: Microban Products Company, Huntersville, NC (US)

( * ) Notice: Subject to any disclaimer, the term of this patent is extended or adjusted under 35 U.S.C. 154(b) by 0 days.

(21) Appl. No.: 15/840,384

(22) Filed: Dec. 13, 2017

(65) Prior Publication Data
US 2018/0171542 A1    Jun. 21, 2018

Related U.S. Application Data

(60) Provisional application No. 62/434,657, filed on Dec. 15, 2016.

(51) Int. Cl.
| | |
|---|---|
| *D06M 15/568* | (2006.01) |
| *A61L 2/00* | (2006.01) |
| *A61L 9/01* | (2006.01) |
| *D06M 11/36* | (2006.01) |
| *D06M 11/44* | (2006.01) |
| *D06M 13/00* | (2006.01) |
| *D06M 15/564* | (2006.01) |
| *D06M 11/42* | (2006.01) |
| *D06M 11/46* | (2006.01) |
| *D06M 101/32* | (2006.01) |

(52) U.S. Cl.
CPC ............. *D06M 11/44* (2013.01); *A61L 2/00* (2013.01); *A61L 9/01* (2013.01); *D06M 11/36* (2013.01); *D06M 13/005* (2013.01); *D06M 15/564* (2013.01); *D06M 11/42* (2013.01); *D06M 11/46* (2013.01); *D06M 2101/32* (2013.01)

(58) Field of Classification Search
CPC ...... D06M 15/00; D06M 15/01; D06M 15/03; D06M 15/17; D06M 15/21; D06M 15/53; D06M 15/564; D06M 15/568; D06M 15/572

See application file for complete search history.

(56) References Cited

U.S. PATENT DOCUMENTS

| | | |
|---|---|---|
| 3,640,675 A | 2/1972 | Thomas |
| 5,508,370 A | 4/1996 | Reiff et al. |
| 6,080,812 A | 6/2000 | Morishima et al. |
| 6,709,709 B1 | 3/2004 | Ozawa et al. |
| 7,175,741 B2 | 2/2007 | West et al. |
| 7,213,309 B2 * | 5/2007 | Wang .................. B32B 5/02 |
| | | 26/28 |
| 7,241,430 B2 | 7/2007 | Graham et al. |
| 7,399,519 B2 | 7/2008 | Fang et al. |
| 7,422,712 B2 | 9/2008 | DeLucia et al. |
| 7,655,112 B2 * | 2/2010 | Koslow ............... B01J 20/2803 |
| | | 162/161 |
| 8,158,155 B2 | 4/2012 | Arehart et al. |
| 8,771,661 B2 | 7/2014 | MacDonald |
| 9,315,937 B2 | 4/2016 | Gedanken et al. |
| 2005/0008608 A1 * | 1/2005 | Parkhurst ............... B01D 53/02 |
| | | 424/76.2 |
| 2005/0084412 A1 | 4/2005 | MacDonald et al. |
| 2005/0084474 A1 * | 4/2005 | Wu ........................ A61L 9/014 |
| | | 424/76.1 |
| 2006/0127335 A1 | 6/2006 | Nakamura |
| 2008/0173216 A1 | 7/2008 | Tsutsui |
| 2010/0189595 A1 | 7/2010 | Webster |
| 2010/0221486 A1 | 9/2010 | Nonninger et al. |
| 2015/0056102 A1 | 2/2015 | Yamada et al. |
| 2015/0272235 A1 | 10/2015 | Ko |
| 2015/0352392 A1 | 12/2015 | Kaiser |
| 2016/0090508 A1 * | 3/2016 | Sworen ............... C08G 18/3218 |
| | | 428/424.4 |

FOREIGN PATENT DOCUMENTS

| | | |
|---|---|---|
| CN | 1756870 A | 4/2006 |
| CN | 103627345 A | 3/2014 |
| CN | 105821648 A | 8/2016 |
| JP | 10-072782 A | 3/1998 |
| JP | 10102378 A * | 4/1998 |
| JP | H10102378 A | 4/1998 |
| JP | 10-219569 A | 8/1998 |
| JP | 2004360084 A | 12/2004 |
| WO | WO 2001/094687 A2 | 12/2001 |

(Continued)

OTHER PUBLICATIONS

Search Report and Written Opinion of corresponding International Application No. PCT/US2017/066302; mailed on May 3, 2018; all enclosed pages cited.
Extended European Search Report, European Application No. 17881111, dated Jul. 20, 2020, 7 pages.
Fan, G-D, "Review of the advances of water-dispersible blocked isocyanates," Journal of Safety and Environment, vol. 12(6): 18-21 (2012).
Guodong, Y. et al., "Water dispersion closed isocyanate research progress", Safety and Environment Journal, vol. 12 (6): 18-21 (2012).
Examination Report for EP Application No. 17881111.3; Issued Jun. 30, 2023 (3 Pages).

(Continued)

*Primary Examiner* — Micah Paul Young
(74) *Attorney, Agent, or Firm* — Shumaker, Loop & Kendrick, LLP

(57) ABSTRACT

A composition for treating a textile fabric to impart an odor control property is provided. The composition has a synergistic effect on controlling odor of a textile fabric for an extended number of home launderings. The composition comprises a urethane based binder dispersion or a urethane precursor in addition to a metal oxide. The composition comprises a blocked isocyanate binder and a metal oxide.

13 Claims, No Drawings

(56) References Cited

FOREIGN PATENT DOCUMENTS

| WO | WO 2003/092885 A2 | 11/2003 |
| WO | WO 2007/040623 A1 | 4/2007 |
| WO | WO 2017/205328 A1 | 11/2017 |

* cited by examiner

ODOR CONTROL COMPOSITION AND TREATMENT METHOD

CROSS-REFERENCE TO RELATED APPLICATION

This application claims priority from U.S. provisional patent application Ser. No. 62/434,657, filed on Dec. 15, 2016, in the United States Patent and Trademark Office. The disclosure of which is incorporated herein by reference in its entirety.

FIELD OF THE INVENTION

The present invention relates to an odor control composition, a method of imparting an odor control property, and a treated article.

BACKGROUND OF THE INVENTION

Textile materials used in apparel tend to generate unpleasant odors due to the metabolic action of microorganisms on human sweat. This causes the breakdown of larger molecules present in sweat, which releases volatile small molecules such as isovaleric acid. Using antimicrobials sometimes is insufficient to control odors in textiles. Furthermore, current odor capturing products for textile finishing treatments are found not durable to home launderings by themselves.

Thus, there is a need for another method of controlling odors in textile fabrics that overcomes the above disadvantages.

SUMMARY OF THE INVENTION

The present invention relates to an odor control composition and a method of imparting an odor control property to an article such as a textile fabric.

In an embodiment of the invention, an odor control composition comprises a metal oxide and a urethane based component selected from the group consisting of a urethane based binder, a urethane precursor, and a combination thereof.

In an embodiment of the invention, an odor control composition comprises a blocked isocyanate binder and a metal oxide.

In an embodiment of the invention, a method of imparting an odor control property to a textile fabric comprises applying a composition comprised of a blocked isocyanate binder and a metal oxide to a textile fabric, and curing the composition.

In an embodiment of the invention, a textile fabric having an odor control property comprises a blocked isocyanate binder and a metal oxide.

Further areas of applicability of the present invention will become apparent from the detailed description provided hereinafter. It should be understood that the detailed description and specific examples, while indicating the preferred embodiments of the invention, are intended for purposes of illustration only and are not intended to limit the scope of the invention.

DESCRIPTION OF THE PREFERRED EMBODIMENTS

The following description of the embodiments of the present invention is merely exemplary in nature and is in no way intended to limit the invention, its application, or uses. The present invention has broad potential application and utility. The following description is provided herein solely by way of example for purposes of providing an enabling disclosure of the invention, but does not limit the scope or substance of the invention.

In an embodiment of the invention, a composition comprises a metal oxide and a urethane based component selected from the group consisting of a urethane based binder, a urethane precursor, and a combination thereof. The composition is particularly suited for treating a textile fabric to impart an odor control property. The composition has a synergistic effect on controlling odor of a textile fabric for an extended number of home launderings.

The metal of the metal oxide includes, but is not limited to, magnesium, silver, copper, zinc, bismuth, titanium, tin, and a combination thereof. Preferred metal oxides are zinc oxide, magnesium oxide, or a combination thereof.

Preferably, a urethane based binder (which, for example, may be a polyurethane based binder) is in a form of a dispersion. Urethane based binder dispersions are typically aqueous, anionic dispersions of high molecular weight aliphatic polyester polyurethanes.

In polyurethane dispersion chemistry, a prepolymer is made from the reaction between an aliphatic polyester polyol and an aliphatic diisocyanate, which is then diluted with acetone. The introduction of anionic groups, such as sulfonates, enables this prepolymer to be dispersed in water. The acetone is removed from the emulsion by distillation and then recycled for further production. Some types of urethane dispersion products can be manufactured through an acetone-free process.

The term "urethane precursor" generally refers to a component that forms a polyurethane binder when polymerized during curing.

In an embodiment of the invention, an odor control composition comprises a blocked isocyanate binder and a metal oxide. The composition is particularly suited for treating a textile fabric to impart an odor control property. The composition has a synergistic effect on controlling odor of a textile fabric for an extended number of home launderings.

The metal of the metal oxide includes, but is not limited to, magnesium, silver, copper, zinc, bismuth, titanium, tin, and a combination thereof. Preferred metal oxides are zinc oxide, magnesium oxide, or a combination thereof.

Blocked isocyanates are typically formed by the reaction of an isocyanate with either an active hydrogen or methylene compound such as malonic esters, or other blocking agents such as alcohols, caprolactams, phenols, oximes, pyrazoles, and malonates.

A preferred blocked isocyanate binder is a water dispersible blocked isocyanate binder. Typical methods of making water dispersible blocked isocyanate can be found, for example, in U.S. Pat. No. 5,508,370. Examples of blocking or capping agents include, but are not limited to, caprolactam (e-cap), methylethylketoxime (MEKO), 3,5-dimethylpyrazole (DMP), and diethyl malonate (DEM). Different blocking agents provide different curing unblocking temperatures during curing and associated storage stability of blocked isocyanate chemistry. The higher the curing temperature, the greater product stability. For the purposes of the present invention, those blocking agents that give a curing temperature between 90° C. to 180° C. can be used. The blocking agents that give a curing temperature between 100°

C. and 170° C. are preferred. More preferred blocking agents are those that have a curing temperature between 110° C. to 160° C.

In an embodiment of the invention, the blocked isocyanate binder may be, for example, anionic or nonionic. The blocked isocyanate dispersion may have a pH range of 5 to 8 for nonionic and a pH range of 7 to 9 for anionic. The viscosity of the blocked isocyanate dispersion at 25° C. (mPas) is preferably in a range of 100 to 300. A solvent of the blocked isocyanate dispersion may include, for example, N-Methyl-2-pyrrolidone (NMP), dipropylene glycol dimethyl ether (DPGDME), and water. Blocked isocyanate dispersions are commercially available.

In an embodiment of the invention, the blocked isocyanate binder is present in a range of 0.05 weight % to 5 weight %, wherein the weight percentage is based on the weight of a dry textile fabric.

In an embodiment of the invention, zinc oxide is present in a range of 0.01 weight % to 10 weight %, wherein the weight percentage is based on the weight of a dry textile fabric.

The textile fabric can be made of various types of fibers including, but not limited to, synthetic fibers, natural fibers, and a combination thereof.

Following are the examples demonstrating the durability of the treatment of the invention. The term "durability", as used herein, generally refers to the ability of an odor control property of a treated textile fabric to withstand an extended number of home launderings.

The composition of the present invention may comprise an antimicrobial. An antimicrobial can be used in addition to the odor capturing formulation of the present invention to further control the odor generation of textile materials. A wide variety of antimicrobials can be used for this purpose including, but not limited to, triclosan, zinc pyrithione, metal salts and oxides, phenols, botanicals, halogens, peroxides, heterocyclic antimicrobials, quaternary ammonium compounds, aldehydes, and combinations thereof.

Other non-limiting examples of additives that can be incorporated in the formulation of the present invention include, but are not limited to, surfactants, dispersants, pH adjusting agents, softeners, wicking aids, and combinations thereof.

In an embodiment of the invention, a method of using a formulation of the invention is provided. The formulation may be applied to a substrate or an article to impart an odor control property.

In an embodiment of the invention, a method of imparting an odor control property to a textile is provided. The method comprises applying a formulation of the invention to a textile material or fabric, and curing the formulation. The curing can be performed in any type of traditional drying oven or stenter range. A curing temperature in a range of 90° C. to 180° C. can be used. A curing temperature in a range of 100° C. to 170° C. is preferred. A curing temperature in a range of 110° C. to 160° C. is more preferred.

The formulation may be applied to a textile material or fabric by any conventional or other technique known to one of ordinary skill in the art including, but not limited to, padding, spraying, roller coating or other types of coating, exhaustion, and combinations thereof. Among them, padding is preferred.

Examples

TABLE 1

Treatment Formulations

| Sample Name | Component | Manufacturer | Weight percentage of each component based on weight of a 100% polyester fabric |
|---|---|---|---|
| Untreated | | | |
| P3 | DP5370 (30% active) | Nyacol Nano Technologies, Inc. | 3 |
| P55 | Trixene 201 (40% active) | Baxenden Chemicals Limited | 0.5 |
| | DP5370 (30% active) | | 3 |
| P56 | Trixene 201 | | 2 |
| | DP5370 | | 1 |
| P57 | Trixene 220 (40% active) | | 2 |
| | DP5370 | | 1 |
| P43 | Trixene 220 | | 0.5 |
| | DP5370 | | 3 |
| P1 | Acrygen APB (45% active) | Omnova Solutions Inc. | 2 |

Trixene is a blocked isocyanate.
Acrygen APB is an acrylic binder.

Testing Performance

Auto regeneration test with isovaleric acid was used to assess odor capturing capacity of a textile material, and energy dispersive x-ray analysis (EDX) was used to evaluate zinc oxide retention on fabric after laundry.

EDX is an instrument used to detect elemental metal on a substrate. An electron beam is used to bombard a target sample for analysis. When the beam of electrons hits the sample, it causes x-rays to be released from the surface of the sample that carry a unique energy signature that are specific to elements found in the sample. These x-rays are detected with the EDX detector to give elemental information about the sample and determine the presence of the element(s) in a substrate quantitatively.

An auto regeneration test is a Gas Chromotography (GC) headspace analytical method developed for gauging the odor capturing activity of a treatment with odor capacity regenerating capability. In accordance with this method, a swatch of fabric measuring 3.6 cm by 3.6 cm was placed in a 20 ml headspace vial with a PTFE septum screw closure. The vial plus textile was heated, open, for 15 minutes at 100 degrees C. The vial was removed from the oven and allowed to cool slightly, then the closure was applied.

One microliter of a solution of isovaleric acid (23.1 mg/ml) in 1:2 ethanol:water was added to the vial through the septum. The vial was then incubated at 60 degrees C. for one hour, and the headspace was sampled and the amount of isovaleric acid present in the headspace gas was measured by Gas Chromatography/Mass Spectrometry (GCMS). The measurement of a vial containing textile (Tm) was compared to that of a vial containing no textile (Te). The percent reduction was calculated as (Te−Tm)/Te*100%. These experiments constituted cycle 0.

In subsequent cycles, new empty vials were prepared, but the same vials containing textiles were re-dosed without opening and subjected to GCMS measurement. There was a two-hour waiting period in which the vials containing textile samples remain closed in between doses of odorant. Multiple cycles may have been performed on the same vial.

TABLE 2

Isovaleric acid odor capture auto regeneration test

| ID | Cycle 0 | Cycle 1 | Cycle 2 | Cycle 3 | Cycle 4 | EDX of Zinc |
|---|---|---|---|---|---|---|
| Untreated polyester fabric, 0HL | 77 | 59 | 33 | 22 | 18 | 72 |
| Untreated polyester fabric, 25HL | 70 | 48 | 36 | 20 | 0 | 55 |
| Treated P3, 0HL | 99 | 98 | 96 | 94 | 93 | |
| Treated P3, 25HL | 74 | 50 | 29 | 16 | 29 | |
| Treated P43, 0HL | 99 | 98 | 95 | 94 | 94 | 7261 |
| Treated P43, 25HL | 97 | 95 | 87 | 81 | 86 | 1816 |
| Treated P55, 0HL | 98 | 96 | 96 | 95 | 92 | |
| Treated P55, 25HL | 91 | 83 | 78 | 69 | 76 | |
| Treated P56, 0HL | 91 | 90 | 89 | 85 | 86 | |
| Treated P56, 25HL | 92 | 86 | 82 | 83 | 82 | |
| Treated P57, 0HL | 94 | 87 | 87 | 86 | 84 | |
| Treated P57, 25HL | 93 | 91 | 86 | 77 | 84 | |
| Treated P1, 0HL | 99 | 97 | 94 | 94 | 93 | 2961 |
| Treated P1, 25HL | 85 | 72 | 74 | 71 | 64 | 315 |

The auto regeneration test showed that the fabric treated with zinc oxide only, without using any binder, has limited capacity to capture isovaleric acid especially during the later cycles of odor exposure. The zinc oxide treatment with binder especially with Trixene, a blocked isocyanate binder, demonstrated excellent odor capturing performance throughout the multiple cycles of odor exposure.

The formulations listed in Table 1 were padded onto the polyester fabric. The application procedure was as follows:

A pad bath was made first by dispersing a formulation such as Trixene and DP5370 in water with let-down targeting the pre-designed application level such as 0.5% and 3%.

The pad bath was padded onto fabrics using a Mathis Horizontal Padder Type HF.

The padded fabrics were cured with a Mathis dryer type LTE-IR. All of the fabrics were cured at 150° C. for 45 seconds.

As used herein, the terms "comprise," "comprising," "include," and "including" are intended to be open, non-limiting terms, unless the contrary is expressly indicated.

As used herein, the terms "composition" and "formulation" are intended to encompass mixtures or solutions having two or more components. These terms are not limiting as to the precise form of solution (e.g. simple solution, suspension, dispersion, colloid), and one of ordinary skill in the relevant art will appreciate that various forms may be employed without departing from the inventive concepts disclosed herein.

As used herein, the terms "biocidal" and like are intended to convey activity against biocidal, antibacterial, antifungal, anti-algae, antiviral, and other pathogenic organisms. The broad biocidal spectrum includes Gram-positive and Gram-negative bacteria, spore and non-spore forming bacteria, viruses, vegetative and non-vegetative fungi, yeast, protozoa, and other microorganisms.

Biocidal activity is intended to mean an inhibiting effect on microbes. Such effects may range from cidal (killing a significant percentage of microbes within a given time period) to static (preventing proliferation, yet not necessarily killing a substantial fraction).

Unless otherwise noted, weight percent (wt. %) is herein expressed as a percent of the total weight of the textile substrate to be treated.

It will therefore be readily understood by those persons skilled in the art that the present invention is susceptible of broad utility and application. Many embodiments and adaptations of the present invention other than those herein described, as well as many variations, modifications and equivalent arrangements, will be apparent from or reasonably suggested by the present invention and the foregoing description thereof, without departing from the substance or scope of the present invention. Accordingly, while the present invention has been described herein in detail in relation to its preferred embodiment, it is to be understood that this disclosure is only illustrative and exemplary of the present invention and is made merely for purposes of providing a full and enabling disclosure of the invention. The foregoing disclosure is not intended or to be construed to limit the present invention or otherwise to exclude any such other embodiments, adaptations, variations, modifications and equivalent arrangements.

What is claimed is:

1. A method of imparting an odor control property of organic odor(s) to a textile fabric, the method comprising:
    applying a composition comprising a blocked isocyanate binder and a metal oxide and a pH adjuster and optionally a softener to a textile fabric, and
    curing the composition applied to the textile fabric thereby forming a treated textile fabric having an organic odor control property that reduces and/or neutralizes odor associated with isovaleric acid (IVA), wherein the treated textile fabric maintains the odor control property after twenty-five home launderings.

2. The method according to claim 1, wherein the blocked isocyanate binder is water dispersible.

3. The method according to claim 1, wherein the blocked isocyanate binder is in a form of a dispersion.

4. The method according to claim 1, wherein a metal of the metal oxide is selected from the group consisting of an oxide of magnesium, silver, copper, zinc, bismuth, titanium, tin, and a combination thereof.

5. The method according to claim 4, wherein the metal oxide is selected from the group consisting of zinc oxide, magnesium oxide, and a combination thereof.

6. The method according to claim 1, wherein the blocked isocyanate binder is present in a range of 0.05 weight % to 5 weight %, wherein the weight percentage is based on weight of a dry textile fabric.

7. The method according to claim 1, wherein the metal oxide is present in a range of 0.01 weight % to 10 weight %, wherein the weight percentage is based on the weight of a dry textile fabric.

8. A textile fabric having an organic odor control property, the textile fabric comprising a composition comprised of a blocked isocyanate binder, a metal oxide, and a pH adjuster and optionally a softener, wherein the textile fabric by reduces and/or neutralizes odor associated with isovaleric acid (IVA), and wherein the textile fabric maintains the odor control property after twenty-five home launderings.

9. The textile fabric according to claim 8, wherein the blocked isocyanate binder is water dispersible.

10. The textile fabric according to claim 8, wherein the blocked isocyanate binder is in a form of a dispersion.

11. The textile fabric according to claim 8, wherein a metal of the metal oxide is selected from the group consisting of magnesium, silver, copper, zinc, bismuth, titanium, tin, and a combination thereof.

12. The textile fabric according to claim 8, wherein the blocked isocyanate binder is present in a range of 0.05 weight % to 5 weight %, wherein the weight percentage is based on weight of the textile fabric when dry.

13. The textile fabric according to claim 8, wherein the metal oxide is present in a range of 0.01 weight % to 10 weight %, wherein the weight percentage is based on the weight of the textile fabric when dry.

* * * * *